(12) United States Patent
Sahasrabudhe

(10) Patent No.: US 7,053,025 B2
(45) Date of Patent: May 30, 2006

(54) PLANT GROWTH STIMULATOR

(75) Inventor: Nirmala Avinash Sahasrabudhe, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 80 days.

(21) Appl. No.: 10/400,074

(22) Filed: Mar. 27, 2003

(65) Prior Publication Data

US 2004/0192550 A1 Sep. 30, 2004

(51) Int. Cl.
*A01N 63/02* (2006.01)
*A01N 63/04* (2006.01)
*A01N 65/00* (2006.01)

(52) U.S. Cl. ...................................... 504/117
(58) Field of Classification Search ............. 504/117; 435/252.1, 252.4, 253.6, 255.2, 255.21, 255.4, 435/255.7

See application file for complete search history.

(56) References Cited

FOREIGN PATENT DOCUMENTS

| JP | 8-322555 | 12/1996 |
| JP | 10-327692 | 12/1998 |
| JP | 11-000065 | 1/1999 |
| WO | 96/24680 | 8/1996 |

OTHER PUBLICATIONS

Liau et al. Derwent Abstract 2000-570996 of TW 385335A. 2000.*
Shokuhin. Derwent Abstract 1997-081073 of JP 8-322555. 2000.*
Sakaguchi. Derwent Abstract 1999-098922 of JP 10-327692. 2000.*
English Language Abstract of JP 8-322555, published Dec. 10, 1996.
English Language Abstract of JP 10-327692, published Dec. 15, 1998.
English Language Abstract of JP 11-000065, published Jan. 6, 1999.
Fontana et al., "*Acetobacter* Cellulose Pellicle as a Temporary Skin Substitute", Applied Biochemistry and Biotechnology, Proceedings of the Eleventh Symposium on Biotechnology for Fuels and Chemicals held May 8-12, 1989 at Colorado Springs, Colorado, vol. 24/25, pp. 253-264 (1990).
J.D. Fontana, "Nature of Plant Stimulators in the Production of *Acetobacter xylinium* (Tea Fungus) Biofilm Used in Skin Therapy", Applied Biochemistry and Biotechnology, Proceedings of the Twelfth Symposium on Biotechnology for Fuels and Chemicals held May 7-11, 1990 at Colorado Springs, Colorado, vol. 28/29, pp. 341-351 (1991).
Blanc, "Characterization of the Tea Fungus Metabolites", Biotechnology Letters, vol. 18, No. 2, pp. 139-142 (1996).
T.S. Yam et al., "Microbiological Activity of Whole and Fractionated Crude Extracts of Tea (*Camellia sinensis*), and of Tea Components", FEMS Microbiology Letters, vol. 12, pp. 169-174 (1997).

* cited by examiner

*Primary Examiner*—S. Mark Clardy
(74) *Attorney, Agent, or Firm*—Greenblum & Bernstein, P.L.C.

(57) ABSTRACT

A plant growth stimulator useful for promoting and maintaining plant growth, wherein said stimulator is post-microbial culture inoculation nutrient medium consisting of black tea and a carbohydrate source, wherein the culture is consisting of *Acetobacter xylinum*, *Candida sp*. and *Zygosaccharomyces rouxii*, and a process for the preparation of the plant growth stimulator, and further, a method of promoting and maintaining the growth of plants using the plant stimulator having multiple disease resistance activity.

20 Claims, No Drawings

PLANT GROWTH STIMULATOR

FIELD OF THE PRESENT INVENTION

A plant growth stimulator useful for promoting and maintaining plant growth, wherein said stimulator is post-microbial culture inoculation nutrient medium consisting of black tea and a carbohydrate source, wherein the culture is consisting of *Acetobacter xylinum, Candida* sp. and *Zygosaccharomyces rouxii*, and a process for the preparation of the plant growth stimulator, and further, a method of promoting and maintaining the growth of plants using a plant stimulator having multiple disease resistance activity.

BACKGROUND AND PRIOR ART OF THE PRESENT INVENTION

In agriculture/horticulture many chemical materials used for improving plant health and productivity, are proving after many years, to have undesirable side effects. Leaving toxic chemical residues on vegetables, fruits or in soil are reported to be toxic to soil and to human health. Many man-made materials do not biodegrade and are proving dangerous to the environment by increasing soil and water pollution. Some herbal materials are found to be useful for increasing plant health and productivity. However, plants take long time to grow and produce the herbal material for commercial use. There is also a constraint on the availability of land to produce such a material. As it is, there is very limited land available for providing food security to increasing population. Under such conditions, microbial preparations prove useful.

In the prior art "Tea fungus" has been used to produce cellulosic Biofilm for medical use-for example as a temporary skin cover in burns and other injuries and the fermented tea left behind has been used as a health drink for human consumption in processes hitherto and described herein below. Acetobacter Cellulose Pellicle as a Temporary Skin Substitute. J. D. Fontana A.M. De Souza, C. K. Fontana, I. L. Torriani, J. C. Moreschi, B. J. Gallotti, S. J. De Souza, G. P. Narsisco, J. A. Bichara and L. F. X. Farah, Applied Biochemistry and Biotechnology, vol 24/25 253–263 (1990). A bacterial strain with morphological properties to *Acetobacterium xylinum* has been cultured in glass vessels in non-agitated inverted sucrose and yeast water based medium for production of thick, smooth and floating cellulosic pellicles. The apyrogenic bacterial biomass, a minor component of the dried biofilm after inactivating by ethylene dioxide had been applied on exuding or bloody tissue. The biofilm displayed several advantages as a biological dressing.

Nature of plant stimulators in the production of *Acetobacter xylinium* (Tea Fungus) Biofilm used in skin therapy. J. D. Fontana, V. C. Franco, S. J. De. Souza, I. N. Lyra and A. M. De Souza, Applied Biochemistry and Biotechnology, vol 28/29.341–351 (1991).

The beneficial role of certain plant extracts in cellulose synthesis was observed. In this work, plant extracts served as substitutes for conventional and co-nutritional sources as yeast or malt extracts. This invention was centered in the nature of compounds arising from such plants as Camellia (commercial tea), *Paullina*, Coffee (unroasted seeds), Theobroma (cacao) Kola or *Sterculia* (cola nut). These plants display, as a common feature, a high content of xanthine based substances. Because of the reduced amount requirement as supplement to carbon source, their infusions were used as low priced ingredients in media formulations. It was found that "tea extract" was a better supplement to 'yeast extract" for producing cellulose pellicle.

Characterization of the "Tea fungus" metabolites. Phillips J. Blanc. Biotechnology Letters, Volume 18 (2), 139–142 (1996).

The symbiotic culture "Tea fungus", traditionally grown on black tea with sucrose for 7 days gives a pleasantly sour and sparkling beverage under aerobic conditions.

The consumption of fermented tea was firstly practiced in 220 B.C. in Manchuria. It then spread to Russia. During the world war II, this beverage was introduced to Germany", then in the 50's, it arrived in France and also in France dominated North Africa, where its consumption was quite popular. Presently, its consumption is popular in United States, this popularity is mainly due to its refreshing power, curative power, presence of vitamin B1, B2, B6 and the antibacterial properties.

Blanc, studied the metabolite formation by "Tea fungus" in presence of 0.1–10.0% sucrose containing media and growing the culture for a period of 0–12 days. The results showed that in the absence of sucrose, acetic acid formation reached the maximum value up to day 5, rapidly decreasing up to day 10. Gluconic acid formation reached maximum at about 7 days and remained steady up to 13 days. With increasing sucrose concentration, there was increase in the gluconic acid formation but decrease in the acetic acid and alcohol synthesis. At 10% sucrose concentration, ethanol concentration rose to a maximum of 1.34 g/l after 5 days of incubation and subsequently decreased. The acetic acid, which was converted from ethanol also, rose to a maximum value of (4.5–6.5 g/l) until the $15^{th}$ day of incubation. He also found that the composition of different fermented tea preparations greatly depended upon the individual tea fungus used from different origins.

Another study, a patent WO 96/24680 (PCT/US96/01846), demonstrated that 'Tea fungus' or fermented tea, produced a material which had inter alia heat resisting and heat insulating properties. This material was used for several applications such as, a burn wound healing material, fire extinguishing material, protecting human body as a fire resistant coating material and as a desalinating material. The spent liquor was used a health drink.

In all these studies the aim was to use the fermented tea for human consumption as a health drink and the fungal biomass mainly as wound cover in the treatment of burns. The use of the said material as health stimulant has been reported.

OBJECTS OF THE PRESENT INVENTION

The main object of the present invention is to develop a plant growth stimulator.

Another main object of the present invention is to develop a process for the preparation of the plant stimulator.

Yet another object of the present invention is to develop a method of stimulating and promoting and maintaining plant growth.

Still another object of the present invention is to develop a multiple-disease resistant plant growth stimulator.

SUMMARY OF THE PRESENT INVENTION

A plant growth stimulator useful for promoting and maintaining plant growth, wherein said stimulator is post-microbial culture inoculation nutrient medium consisting of black tea and a carbohydrate source, wherein the culture is consisting of *Acetobacter xylinum, Candida* sp. and *Zygosac-*

*charomyces rouxii*, and a process for the preparation of the plant growth stimulator, and further, a method of promoting and maintaining the growth of plants using the plant stimulator according to the present invention having multiple disease resistance activity.

DETAILED DESCRIPTION OF THE PRESENT INVENTION

A plant growth stimulator useful for promoting and maintaining plant growth, wherein said stimulator is post-microbial culture inoculation nutrient medium consisting of black tea and a carbohydrate source, wherein the culture is consisting of *Acetobacter xylinum, Candida* sp. and *Zygosaccharomyces rouxii*, and a process for the preparation of the plant growth stimulator, and further, a method of promoting and maintaining the growth of plants using the plant stimulator according to the present invention having multiple disease resistance activity.

In main another embodiment of the present invention, wherein a plant growth stimulator useful for promoting and maintaining plant growth, said stimulator is post-microbial culture inoculation nutrient medium consisting of black tea and a carbohydrate source, wherein the culture is consisting of *Acetobacter xylinum, Candida* sp. and *Zygosaccharomyces rouxii*, In still another embodiment of the present invention, wherein a process for the preparation of the plant growth stimulator, said process comprising steps of:
  preparing nutrient medium comprising black tea and a carbohydrate source,
  inoculating microbial mixture consisting of bacterium *Acetobacter xylinum*, and yeasts *Candida* sp. and *Zygosaccharomyces rouxii* to the nutrient medium to obtain a culture,
  maintaining culture in a stationary phase for about 3–8 days at room temperature, and
  separating the biomass from the culture to obtain plant growth stimulator.

In still another embodiment of the present invention, wherein nutrient medium comprises a carbohydrate source of concentration ranging between 0.5–10%, and black tea powder of concentration ranging between 0.1 to 1.5% in water.

In still another embodiment of the present invention, wherein the pH of the medium is ranging between 4.0 to 5.0.

In still another embodiment of the present invention, wherein the tea is obtained from plant *Camellia saneness*.

In still another embodiment of the present invention, wherein the carbohydrate source is sucrose.

In still another embodiment of the present invention, wherein the concentration of carbohydrate is 2.5%.

In still another embodiment of the present invention, wherein concentration of tea powder is about 0.5%.

In still another embodiment of the present invention, wherein the room temperature is about 30° C.

In still another embodiment of the present invention, wherein maintaining the culture for about 6 days.

In still another embodiment of the present invention, wherein the stimulator shows golden yellow color due to carbohydrate.

In still another embodiment of the present invention, wherein the carbohydrate is utilized in first two days of the incubation.

In still another embodiment of the present invention, wherein a method of promoting and maintaining the growth of plants using the plant stimulator according to the present invention having multiple disease resistance activity, said method comprising the steps, of:
  diluting the stock solution of stimulator with water,
  spraying the diluted stimulator on the plants, and
  obtaining plants of increased growth having multiple-disease resistance.

In still another embodiment of the present invention, wherein said stimulator promoting flower and fruit growth both qualitatively and quantitatively.

In still another embodiment of the present invention, wherein the dilution is ranging between 0.2 to 5%.

In still another embodiment of the present invention, wherein the stimulator is used as plant foliar spray.

In still another embodiment of the present invention, wherein the stimulator is to be used about 1–5 times.

In still another embodiment of the present invention, wherein the stimulator shows activity after about two sprays.

In still another embodiment of the present invention, wherein the minimum of three sprays are required for desired changes.

In still another embodiment of the present invention, wherein the stimulator provides multiple disease resistance to plants.

In still another embodiment of the present invention, wherein the diluted material is a mixture of organic acids, and low molecular weight ploy phenols.

In still another embodiment of the present invention, wherein the stimulator is used at an interval of about 7–18 days.

In still another embodiment of the present invention, wherein the microbial mixture can be stored and transported in dry form and used by diluting in water for about 25–35 minutes.

In still another embodiment of the present invention, wherein the tea contributes to multiple disease resistance activity of the stimulator.

In still another embodiment of the present invention, wherein the stimulator is active for about 100 days.

In still another embodiment of the present invention, wherein the stalk diameter of the plant doubles.

In still another embodiment of the present invention, wherein the flower diameter increases by about 60–70%.

In still another embodiment of the present invention, wherein the flower bud emergence is as high as about 98%.

In still another embodiment of the present invention, wherein the leaves of the plant shine with more luster.

In still another embodiment of the present invention, wherein the number of flowers per plant increases by about 150–200%.

In still another embodiment of the present invention, wherein all the flowers bloom at one time.

In still another embodiment of the present invention, wherein this invention relates to fungus inoculated plant health stimulator. More particularly it relates to the said material having plant health stimulating, flower and fruit promoting activity useful for maintaining plants in a healthy state and improving plant quality and quantity of flowers and fruits useful in horticulture, floriculture and nurseries. Still more particularly it relates to the said material comprising fungus inoculated Tea.

The present invention there is provided a low cost method for preparation of a material to improve plant health, productivity and quality of flowers and fruits.

The method comprises preparing a nutrient medium in which "Tea fungus" will grow, adding a starter culture of "Tea Fungus" to the nutrient medium. Growing the culture on the surface of the nutrient medium and separating the material from the culture.

In still another embodiment of the present invention, wherein "Tea Fungus" is essentially a mixture of a bacterium *Acetobacter xylinum* and yeasts: *Candida* sp. and *Zygosaccharomyces rouxii* in sugar tea. "Tea fungus" term probably arises from the bacterium's ability to synthesize a floating cellulose network that resembles a surface mold growing on non-agitated liquid media.

Accordingly, the present invention provides obtaining a fungus inoculated plant health stimulator comprising of preparing a nutrient medium in stainless steel vessel, adding a culture, maintaining in a stationary phase for 2–8 days at a room temperature, growing the culture on the surface of the nutrient medium in plastic containers, separating the biomass from the culture, to obtain the plant health stimulator.

In a feature of the present invention the nutrient medium contains a carbohydrate source having concentration of 0.5 to –10% exemplified by sucrose and black tea powder 0.1 to 1.5% in water at a pH ranging between 4 to 5.0.

In another feature of the present invention the stock solution is diluted before use with water as given in Table-1:

TABLE 1

| Plant | % Dilution |
|---|---|
| Rose sp. | 1.0 to 2.0 |
| Jasmin sp | 0.5 to 1.0% |
| Mango sp | 0.5 to 1.0% |

The above dilutions are for illustrative purpose only and should not be construed the limit of the Scope of Invention.

In still another feature the diluted material may be used as a plant folier spray, Regular use of this material helps plants to acquire disease resistance to remain healthy. The diluted material thus prepared is a mixture of organic acids and low molecular weight ploy phenols. After spraying in very dilute form, it helps plants to acquire multiple disease resistance and enhances plant health and productivity with respect to flowers and fruits The fungus is cultured or cultivated from a pre-culture, or a starter culture of the fungus in closed plastic boxes having a bottom wall and a peripheral side walls upstanding from the bottom wall. The preferred nutrient medium is an aqueous extract of the black tea powder that is conventionally used for drinking(i.e. leaves from the plants *Cameillia saneness*) with a carbohydrate such as, sugar dissolved therein. Typically the aqueous tea extract contains 2.5% by weight of sugar and 0.5% by weight of tea powder. This provides an adequate nutrient medium. Tea is prepared using filtered tap water in a stainless steel vessel. The fungus is preferably cultured in plastic boxes, at room temperature ranging from 15 to 40° C., preferably at 30° C. for at least 3 days, preferably 6 days.

The optimum conditions and parameters under which the fungus is cultured may be determined by routine experimentation by a person skilled in the art. When the color of the medium turns golden yellow and imparts acidic smell, the material is separated from the fungal mass. Part of the fungus may be sun dried and preserved. When required, it is immersed in water for about 30 minutes to form a gel like material and can be a starter. The plant health stimulator provided by the present invention is also used to increase plant health and productivity. In general following improvements were observed in the plant health, and productivity.

This liquid is used as a plant foliar spray after suitable dilution regularly with an interval of 15 days.

Part of the "Tea fungus" may be commuted to form a dry film after sun drying and when required, it is immersed in water for about 30 minutes and used as a starter culture when required. Remaining material can be used as an adsorbent to sediment the colloidal particles from industrial effluent.

The invention is illustrated by the following examples, which should not be construed to limit the scope of the present invention.

EXAMPLE 1

The nutrient medium was prepared by adding 2.5% w/v cane sugar and 0–1.5% w/v of black tea powder, to boiling tap water and immediately removing from the gas-stove, covering with lid and allowing to cool to room temperature, filtering through a muslin cloth, inoculating with fungus and culturing it away from the sun-light or heat. The maximum sugar concentration required for growth of the fungus was 2.5%. In the absence of sugar, color of the medium did not turn to golden yellow or impart acidic smell. Under the sugar stress, the fungus synthesized red color pigment and fermented tea did not show increase in plant productivity, when sprayed on plants.

EXAMPLE 2

The nutrient medium was prepared by adding black tea powder of any brand in 0.5% w/v concentration. In the absence of black tea, the fermented medium did not show antimicrobial activity and increase in plant productivity. Concentration of tea was not found to be very critical. Minimum tea concentration of 0.5% w/v was found to be adequate to get golden color liquid with acidic smell.

EXAMPLE 3

The nutrient medium was inoculated with "Tea fungus" and incubated for 8 days. Sugar utilization was complete within 48 hours. However, the fermented material did not show improvement in plant productivity in turns of flowers or fruits. The optimum incubation period was found to be 6 days. (This was found to be inoculum dependent).

The majority of plants revealed good results with 1.100 dilution. Some varieties of rose, and mango required 1:50 proportion. The fermented tea was filtered through muslin cloth and stored for 8–90 days before application.

The material remained active up to 90 days. Afterwards the material lost its

EXAMPLE 4

The fermented material after proper dilution when sprayed on flowering plants, for 1–5 times at the interval of 8–15 days, showed improvement in plant health, vigor and productivity; After 2 sprays visible change was seen in the plant health and color. Minimum 3 sprays are required to get increase in the number of flower buds. There was also increase in the size of flowers and in the flower stocks. The healthy flowers remained fresh for a longer period on plants as well as in flower vase. These results are summarized in Table 2.

TABLE 2

Characteristics of leaves, flowers and flower stalks with application of the material

| Plant | Untreated | Treated |
|---|---|---|
| Jasmin (Mogara) | 40 flowers/plant | 100 flowers/plant |
| Aboli | 5–6/inflorescence | 10–12/inflorescence |
| *Hibiscus Jaswandi*) | 35–40 flowers/plant | 150–200 flowers/plant |
| Exora | A bunch of flowers with ~3 cm | A bunch of flowers with ~6.5 cm diameter/branch |
| Gerbera | | |
| Flower diameter | ~5.0 cm | 8.0–8.5 cm |
| Stalk diameter | 0.4 cm | 0.7~0.8 cm |
| Life on plants/vase | 7 days | 10 days |
| Rose | | |
| Leaves | Tender, dark green to red, no luster | Tender, light, green or light red, shining with luster |
| Flower bud Emergence | 25% | 98% |
| Flower diameter | 3.5 cm | 5.0–5.5 cm |
| Stalk diameter | 0.5 cm | 1.0 cm |
| Life on plant/vase | 6 days | 9–11 days |

EXAMPLE 5

The health and flower promoting activity of the material was tested on rose plants. Total ten beds, each having ten plants were selected for this trial. One month after spurning, total 50 plants were sprayed with the material (One liter tap water received: 10–20 cc of the material) after every 15 days. Remaining 50 plants did not receive the material and served as control for comparison Results are summarized in table 2.

EXAMPLE 6

In order to test the material for its health, flower and fruit promoting activity in case of mango plant, a thirty-year old mango tree from the applicants garden was selected. The material was diluted and sprayed on this plant fourteen times with 15 days interval during two consecutive seasons. The old tree bearing about one hundred fruits per year showed visible change in the color and texture of leaves; number of inflorescence bearing female flowers and quality and quantity of fruits.
1. The leaves were light green, smooth, tender and shining with luster.
2. The tip of every branch produced inflorescence containing more number of female flowers.
3. All the flowers bloom at one time.
4. Numbers of fruits were initially about 400 and 800 in two seasons respectively.
5. Fruits occurred in the bunches of average 4–6 and 6–8 respectively.
6. At the time of harvest, the author collected about 300 and 700 fruits in two seasons respectively.

The invention claimed is:

1. A method of promoting and maintaining growth of plants using a plant stimulator composition having multiple disease resistance activity, the stimulator composition comprising a post-microbial culture inoculation nutrient medium composed of black tea and a carbohydrate source, wherein the culture comprises *Acetobacter xylinum, Candida* sp. and *Zygosaccharomyces rouxii*, said method comprising:

diluting a stock solution of the stimulator composition with water;

spraying the diluted stimulator composition on the plants, and obtaining plants of increased growth having multiple-disease resistance.

2. The method according to claim 1, wherein the nutrient medium comprises a carbohydrate source of concentration ranging between 0.5–10% w/v, and black tea powder of concentration ranging between 0.1 to 1.5% w/v in water.

3. The method according to claim 1, wherein the nutrient medium comprises a carbohydrate source of concentration of about 2.5% w/v, and black tea powder of concentration of about 0.5% w/v in water.

4. The method according to claim 1, wherein said stimulator composition promotes flower and fruit growth both qualitatively and quantitatively.

5. The method according to claim 1, wherein the dilution ranges between 0.2 to 5%.

6. The method according to claim 1, comprising spraying the stimulator composition on foliage.

7. The method according to claim 1, wherein the stimulator composition is sprayed about 1–5 times on the plants.

8. The method according to claim 1, wherein the stimulator composition shows activity after about two sprays.

9. The method according to claim 1, wherein a minimum of three sprays are required for desired changes.

10. The method according to claim 1, wherein the stimulator composition provides multiple disease resistance to plants.

11. The method according to claim 1, wherein the diluted material is a mixture of organic acids, and low molecular weight polyphenols.

12. The method according to claim 1, wherein the stimulator composition is sprayed on the plants at an interval of about 7–18 days.

13. The method according to claim 1, wherein the stimulator composition is stored and transported in dry form and used by diluting in water for about 25–35 minutes.

14. The method according to claim 1, wherein the stimulator composition is active for about 100 days.

15. The method according to claim 1, wherein spraying comprises spraying to achieve a doubling of plant stalk diameter.

16. The method according to claim 1, wherein the spraying comprises spraying to achieve a flower diameter increase of about 60–70%.

17. The method according to claim 1, wherein spraying comprises spraying to achieve a flower bud emergence as high as about 98%.

18. The method according to claim 1, wherein the spraying comprising spraying the leaves of the plant to obtain leaves having increased luster.

19. The method according to claim 1, wherein the spraying comprises spraying to achieve an increase in a number of flowers per plant increases of about 150–200%.

20. The method according to claim 2, wherein the spraying comprises spraying to obtain blooming of all flowers at one time.

* * * * *